US00PP21073P2

(12) United States Plant Patent
Toyama

(10) Patent No.: US PP21,073 P2
(45) Date of Patent: Jun. 22, 2010

(54) CHERRY TREE NAMED 'PC7903-2'

(50) Latin Name: *Prunus avium*
Varietal Denomination: PC7903-2

(75) Inventor: Thomas K. Toyama, Eugene, OR (US)

(73) Assignee: Washington State University Research Foundation, Pullman, WA (US)

( * ) Notice: Subject to any disclaimer, the term of this patent is extended or adjusted under 35 U.S.C. 154(b) by 276 days.

(21) Appl. No.: 11/818,891

(22) Filed: Jun. 14, 2007

Related U.S. Application Data

(60) Provisional application No. 60/815,789, filed on Jun. 21, 2006.

(51) Int. Cl.
*A01H 5/00* (2006.01)

(52) U.S. Cl. ..... Plt./181

(58) Field of Classification Search ..... Plt./181
See application file for complete search history.

*Primary Examiner*—Kent L Bell
(74) *Attorney, Agent, or Firm*—Michelle Bos

(57) ABSTRACT

A new cultivar of sweet cherry tree named 'PC7903-2' is disclosed. The new cultivar is notable for its very large, juicy fruit.

1 Drawing Sheet

Latin name of the genus and species of the plant claimed: *Prunus avium.*

Variety denomination: 'PC7903-2'.

BRIEF DESCRIPTION OF THE PHOTOGRAPHS

The photograph shows the fruit of the new cultivar.

DETAILED BOTANICAL DESCRIPTION OF THE VARIETY

The present invention relates to a new variety of sweet cherry tree named 'PC7903-2.' 'PC7903-2' was developed at the Washington State University Irrigated Agriculture Research and Extension Center (I.A.R.E.C.) at Prosser, Wash. It was selected from among several seedlings that resulted from a controlled cross of 'PC7147-4' (female parent, not patented) and 'PC7146-11' (male parent, not patented) made in 1979, and has continued to be tested as 'PC7903-2.' 'PC7903-2' was first asexually propagated by grafting in 1981 at Prosser, Wash.

All second and third generation test trees observed closely have shown no tendency toward the 'cherry crinkle-leaf' genetic disorder which is common in 'Bing,' (unpatented variety) as well as in several other varieties of sweet cherry.

Asexual reproduction of this new and distinct cultivar at test facilities near Prosser shows that its desirable characteristics come true to form and are established and transmitted through succeeding propagations by grafting.

'PC7903-2' is a 'Bing' type cherry, and is distinguished from 'Bing' and 'PC8007-2' (U.S. Plant Patent Pending, Ser. No. 11/895,279), a similar 'Bing' type variety, by several characteristics, as set forth in the table below.

| | 'PC7903-2' | 'PC8007-2' |
|---|---|---|
| Bloom Date | 2 days after 'Bing' | 6 days after 'Bing' |
| Harvest Date | Similar to 'Bing' | 6 to 10 days before 'Bing' |

'PC7903-2' is further distinguished from 'Bing' and other 'Bing'-type varieties by its tremendous capacity to set fruiting spurs near the tip of two year old fruiting wood.

The following is a detailed botanical description of 'PC7903-2,' based on observations made during the 2004, 2005, 2007 and 2009 growing seasons in Prosser, Wash. of trees planted in 1981 on Mazzard rootstock. It should be understood that the botanical and analytical characteristics described will vary somewhat depending upon cultural practices and climatic conditions, and can vary with location and season. Color descriptions are made with reference to The Royal Horticultural Society Colour Chart. Quantified measurements are expressed as an average of measurements taken from a number of individual plants of the new variety. The measurements of any individual plant, or any group of plants, of the new variety may vary from the stated average.

Tree: Vigorous, precocious; Upright, moderate branching; Medium-dense, Height 4.6 m; Spread 3.4 m;

*Trunk.*—Diameter 41 cm at 15 cm above soil, bark moderately rough, bark color 199D, trunk lenticel color 197A, trunk lenticel size 11.4 mm; Very productive, Annual bearer; not self fertile, acceptable pollenizers include 'Bing', 'Van' (not patented), 'Rainier' (not patented) and 'PC7144-6' (U.S. Plant Pat. No. 11,385)

Branches:

2 *year old fruiting branch.*—Length 29 cm, diameter at mid-point 5.3 mm; crotch angle about 45 degrees, branch texture smooth, color 183B and 199A; Lenticels shape round or elongated, width 0.5 to 1.0 mm, length 1.0 to 2.4 mm, color greyed-orange 165A, density 9 to 14 per $cm^2$.

One-year old shoot:

*New branch growing from scaffold.*—Length 59 cm, diameter 5 mm (varies significantly); texture smooth; Color yellow-green 145A.

*Lenticels.*—Round, 0.1 to 0.5 mm diameter, color white 155D, density 10 to 15 per $cm^2$; vegetative bud held out in relation to shoot.

Leaf:

*Size.*—Length 13.3 cm, width 6.3 cm, ratio of length to width 2.1, thickness 0.2 mm.

*Texture.*—Upper surface mostly smooth, leathery, lower surface smooth.

*Shape.*—Elliptic, tip acute, base rounded, margin serrated.

*Color.*—Upper surface dark green 141A, lower surface dark green 141C.

*Midvein.*—Width 1.4 mm, upper surface color green 145C, lower surface color green 145C.

*Petiole.*—Length 4.0 cm, width 2.0 cm, ratio of petiole length to blade length 0.38, petiole upper surface color light red 166A, lower surface color light red 166B.

*Nectaries.*—Present, quantity 2, length 1.7 mm, width 1.2 cm, color 185A, kidney shaped.

Flower buds: 4 to 8 per spur; shape conical; length 8.2 mm, diameter 5.3 mm; color 177A greyed-orange.

Flower: Large, diameter 2.8 cm, depth 4.5 mm; petals broad elliptic, free to overlapping; petal length 16 mm, petal width 15 mm, margin smooth, apex emarginate; color white (upper and lower surface); First bloom date 2 days later than 'Bing'; Full bloom date 2 days later than 'Bing'.

*Pedicel.*—Length 21.1 mm, diameter 0.9 mm, color green 143C.

Reproductive organs:

*Pistil.*—Style length 12.9 mm, diameter 0.5 mm, color yellow-green 151A; Stigma diameter 1.1 mm, stigma shape elliptic club, stigma color yellow-green N144A; Ovary length 2.9 mm, diameter 1.7 mm, color green 143A.

*Stamens.*—40 per flower.

*Anther.*—Diameter 1 mm at widest point, heart shaped, color greyed-orange 163B.

*Filament.*—Length 8.1 mm, color white 155C.

*Sepals.*—5 per flower, length 5.4 mm, width 4.3 mm, shape elliptical, apex obtuse, base truncate, margin smooth, color upper surface green 138A with highlights of greyed-red 178A, color lower surface yellow-green 144A.

Fruit: 1 to 3 per cluster, very large, apical diameter 23.8 mm, axial diameter 26 mm, weight 9.5 g; shape cordate, asymmetrical; pistil end pointed; suture indistinct; stalk cavity width 13.2 mm, depth 4.2 mm; skin smooth, tenacious to flesh, thin (less than 0.2 mm), color red-purple 59A, lenticels small, abundant; flesh firm, slightly fibrous, melting, color dark red 53A, very juicy; stem length 4.0 cm, thickness 1.5 mm; abscission layer present; eating quality excellent Fruit analytical data:

Fruit Data for 'PC7903-2' (Jun. 29, 2009)

| Trait | Machine reading/sensory score |
|---|---|
| % Brix | 15 |
| Titratable acidity (%) | 0.99 |
| Astringency | 1 (0-5 scale) |
| Bitterness | 2 (0-5 scale) |
| Flavor | 1 (0-5 scale) |

Stone: Length 11 mm, width 10.5 mm, thickness 8.9 mm; shape broad elliptic, rounded apex and base; texture smooth; no tendency to split; color greyed-yellow 161D Kernel: Length 8 mm, width 6.1 mm, thickness 5.0 mm; shape ovate, somewhat oblique, apex acute, base rounded; color greyed-yellow 162D with filamentous stripes of greyed orange 164B, almond-like taste, moderate intensity,

*Viability.*—Appears fully developed, healthy.

Time of fruit maturity: Medium, late June or early July (Jul. 1, 2009 at Prosser, Wash.)

Disease/pest resistance/susceptibility: None noted

Market use: Fresh

I claim:

1. A new and distinct cherry tree, substantially as shown and described herein.

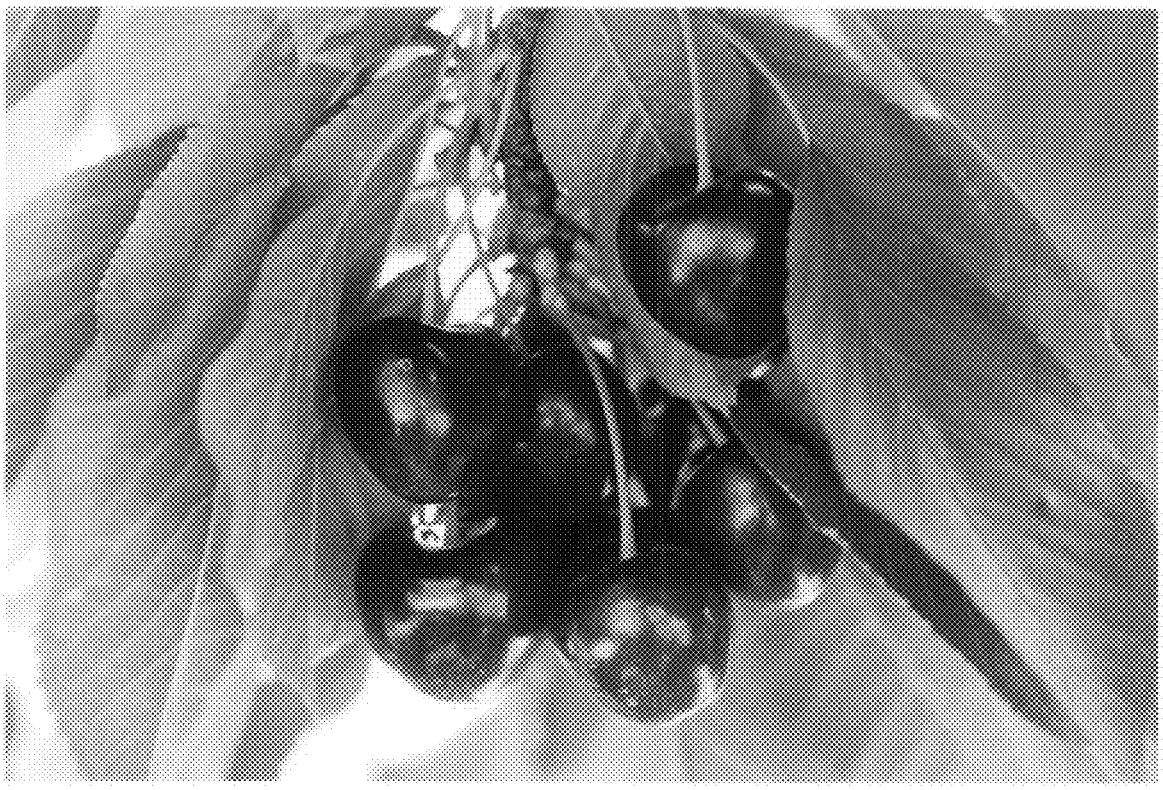

* * * * *